(12) United States Patent
Lee

(10) Patent No.: US 6,546,073 B1
(45) Date of Patent: Apr. 8, 2003

(54) SYSTEMS AND METHODS FOR GLOBAL OPTIMIZATION OF TREATMENT PLANNING FOR EXTERNAL BEAM RADIATION THERAPY

(75) Inventor: Eva K. Lee, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 60 days.

(21) Appl. No.: 09/706,915

(22) Filed: Nov. 6, 2000

Related U.S. Application Data

(60) Provisional application No. 60/164,029, filed on Nov. 5, 1999.

(51) Int. Cl.[7] .............................................. A61N 5/10
(52) U.S. Cl. ........................................ 378/65; 378/901
(58) Field of Search .............................. 378/64, 65, 901

(56) References Cited

U.S. PATENT DOCUMENTS

| | | | |
|---|---|---|---|
| 5,027,818 A | 7/1991 | Bova et al. ............ 128/653 R |
| 5,373,844 A | 12/1994 | Smith et al. ............. 128/653.1 |
| 5,458,125 A | 10/1995 | Schweikard ............ 128/653.1 |
| 5,555,283 A | 9/1996 | Shiu et al. .................. 378/151 |
| 5,602,892 A | 2/1997 | Llacer ......................... 378/65 |
| 5,748,700 A | 5/1998 | Shepherd et al. ............. 378/65 |
| 5,815,547 A | 9/1998 | Shepherd ..................... 378/65 |
| 5,879,281 A | 3/1999 | Ein-Gal .......................... 600/1 |
| 5,945,684 A | 8/1999 | Lam et al. ................ 250/492.3 |
| 6,044,126 A | 3/2000 | Rousseau et al. ............. 378/65 |
| 6,260,005 B1 * | 7/2001 | Yang et al. .................... 703/11 |

\* cited by examiner

*Primary Examiner*—David V. Bruce
(74) *Attorney, Agent, or Firm*—Thomas, Kayden, Horstemeyer & Risley, LLP

(57) ABSTRACT

Systems and methods for providing an optimal treatment plan for delivering a prescribed radiation dose to a predefined target volume within a patient using an external beam radiation delivery unit are provided. The systems have an interface which is adapted to receive information related to a prescribed radiation dose, a predefined target volume within a patient, and parameters associated with an external beam delivery unit. The systems also have a treatment plan modeling processor which is adapted to receive all of the input data and develop a dose calculation optimization model defining a global system. The systems also have an optimization processor which is adapted to determine an optimal treatment plan based on the dose calculation optimization model and all the input data. The methods involve (1) receiving information related to the prescribed radiation dose, the predefined target volume, and parameters associated with the external beam delivery unit, (2) developing a dose calculation optimization model based on a plurality of variables corresponding to the information which define a global system, and (3) outputting an optimal treatment plan based on the dose calculation optimization model and the information.

27 Claims, 4 Drawing Sheets

SYSTEMS AND METHODS FOR GLOBAL OPTIMIZATION OF TREATMENT PLANNING FOR EXTERNAL BEAM RADIATION THERAPY

CROSS REFERENCE TO RELATED APPLICATION

This application claims the benefit of U.S. Provisional Application No. 60/164,029, filed Nov. 5, 1999, which is also incorporated herein by reference.

FIELD OF THE INVENTION

The present invention relates generally to treatment planning for external beam radiation therapy, and more particularly, to systems and methods for global optimization of treatment planning for external beam radiation therapy.

BACKGROUND OF THE INVENTION

External beam radiation therapy is a well-known treatment option available to the radiation oncology and neurosurgery communities for treating and controlling certain central nervous systems lesions, such as arteriovenous malformations, metastatic lesions, acoustic neuromas, pituitary tumors, malignant gliomas, and other intracranial tumors. As the name implies, the procedure involves the use of external beams of radiation directed into the patient at the lesion using either a gamma unit (referred to as a Gamma Knife), a linear accelerator, or similar beam delivery apparatus. Although treating the lesions with the radiation provides the potential for curing the related disorder, the proximity of critical normal structures and surrounding normal tissue to the lesions makes external beam radiation therapy an inherently high risk procedure that can cause severe complications. Hence, the primary objective of external beam radiation therapy is the precise delivery of the desired radiation dose to the target area defining the lesion, while minimizing the radiation dose to surrounding normal tissue and critical structures.

The process of treating a patient using external beam radiation therapy consists of three main stages. First, a precise three-dimensional map of the anatomical structures in the location of interest (target volume) is constructed using any conventional three-dimensional imaging technology, such as computed tomography (CT) or magnetic resonance imaging (MRI). Second, a treatment plan is developed for delivering a predefined dose distribution to the target volume that is acceptable to the clinician. Finally, the treatment plan is executed using an accepted beam delivery apparatus.

Thus, the basic strategy of external beam radiation therapy is to utilize multiple beams of radiation from multiple directions to "cross-fire" at the target volume. In that way, radiation exposure to normal tissue is kept at relatively low levels, while the dose to the tumor cells is escalated. Thus, the main objective of the treatment planning process involves designing a beam profile, for example, a collection of beams, that delivers a necrotic dose of radiation to the tumor volume, while the aggregate dose to nearby critical structures and surrounding normal tissue is kept below established tolerance levels.

One existing method for treatment planning in external beam radiation therapy is standard manual planning. This method is referred to as forward planning because the physician solves the direct problem of determining the appropriate dose distribution given a known set of beam characteristics and beam delivery parameters. In other words, standard manual planning involves a trial-and-error approach performed by an experienced physician. The physician attempts to create a plan that is neither complex nor difficult to implement in the treatment delivery process, while approximating the desired dose distribution to the greatest extent possible. For instance, the physician may choose how many isocenters to use, as well as the location in three dimensions, the collimator size, and the weighting to be used for each isocenter. A treatment planning computer may calculate the dose distribution resulting from this preliminary plan. Prospective plans are evaluated by viewing isodose contours superimposed on anatomical images and/or with the use of quantitative tools such as cumulative dose-volume histograms (DVH's).

Standard manual planning has many disadvantages. This iterative technique of plan creation and evaluation is very cumbersome, time-consuming, and far from optimal. Thus, manual planning results in much higher costs for patients and insurers. The physician or other experienced planner can evaluate only a handful of plans before settling on one. Thus, standard planning has very limited success in improving local tumor control or reducing complications to normal tissue and critical structures, and as a result, greatly limits the quality-of-life for patients. In standard manual planning, there is no mechanism for allowing the advance imposition of clinical properties, such as, for example, an upper bound on dose received by normal tissue or the specific shape of dose-response curves to the tumor and to critical structures, on the resulting plans. Furthermore, manual planning is subjective, inconsistent, far from optimal, and only enables a small amount of treatment plans to be examined by the physician.

Another method for treatment planning in external beam radiation therapy employs computer systems to optimize the dose distributions specified by physicians based on a set of preselected variables. This approach is known as inverse planning in the medical community because the computer system is used to calculate beam delivery parameters that best approximate the predetermined dose, given a set of required doses, anatomical data on the patient's body and the target volume, and a set of preselected or fixed beam orientation parameters and beam characteristics. In order to solve the complex problem of arriving at an optimal treatment plan for the domain of possible variables, all existing methods of inverse treatment planning fix at least a subset of the set of variables. For example, a particular modality of external beam radiation therapy may include the following domain of possible variables: (1) number of beams, (2) configuration of beams, (3) beam intensity, (4) initial gantry angle, (5) end gantry angle, (6) initial couch angle, (7) end couch angles, (8) prescription dose, (9) target volume, and (10) set of target points. State of the art inverse treatment planning approaches preselect a subset of these variables and fix them during the optimization calculation.

Despite its obvious advantages over the standard manual approach, existing inverse treatment planning approaches have several disadvantages and inadequacies. As described above, these approaches do not incorporate each of the domain of possible variables into the optimization calculation. Instead, these approaches fix at least a subset of these variables to arrive at an "optimal" treatment plan. This type of "local optimization" is inherently problematic because it does not allow the full flexibility of choosing different, beam geometries, beam orientation parameters, and beam parameters, imposing dose limits, and placing constraints on physical planning parameters. In other words, these approaches do not enable "global optimization" of treatment planning for external beam radiation therapy. Therefore, these approaches are limited by "less than optimal" treatment plans and, consequently, are unable to adequately control tumor growth or reduce normal tissue complications. Furthermore, there are an infinite number of possible treatment plans in inverse treatment planning, and existing methods only look at a small subset of potential plans and select the "best" from the subset. Thus, the resulting treatment plan is not a globally optimal plan.

Furthermore, existing inverse treatment planning are not well-suited for use with newer external beam radiation therapy modalities. Recent technological advances have resulted in sophisticated new devices and procedures for external beam radiation delivery, such as, for example, high-resolution multi-leaf collimators, intensity-modulated radiation therapy (IMRT), and non-coplanar arc stereotactic radiosurgery (NASR). Unlike conventional radiation therapy where radiation profiles are altered via the use of a limited number of wedges, beam blocks and compensating filters, these new devices and procedures allow a large collection of beams to be shaped in any desired fashion with regard to both the geometrical shape and fluence across the field to create fixed or moving nonuniform beams of photons or charged particles. While the flexibility and precise delivery capability resulting from these advances is clearly advantageous, their full potential cannot be realized using "local optimization" schemes which do not incorporate each of the domain of possible variables into the optimization calculation, but instead fix at least a subset of these variables to arrive at an "optimal" treatment plan.

Thus, an unaddressed need exists in the industry to address the aforementioned deficiencies and inadequacies.

SUMMARY OF THE INVENTION

The present invention solves the problems described above by providing systems and methods for providing a globally optimal treatment plan for delivering a prescribed radiation dose to a target tumor volume within a patient using an external beam radiation source. The present invention enables a physician performing external beam radiation therapy to develop a globally optimal treatment plan, which results in improved patient care and improved efficiency. For example, in the field of external beam radiation therapy, the present invention reduces normal tissue complications, improves tumor control, enables physicians to evaluate a set of globally optimal solutions, reduces the time and cost associated with producing a treatment plan, eliminates trial and error visual optimization, enables physicians to perform radiation therapy in complex situations, such as where critical structures are near the tumor, improves the percentage of tumor volume covered by a prescription isodose line, reduces the ratio of the maximum dose to the prescribed dose, improves the ratio of the volume of the prescribed isodose surface to the target volume, and improves the ratio of the maximum dose received by normal tissue to the prescribed dose.

Briefly described, the systems according to the present invention for providing an optimal treatment plan have three main components. The systems have an interface which is adapted to receive information related to a prescribed radiation dose, information related to a predefined target volume within a patient, and information related to parameters associated with an external beam delivery unit. The systems also have a treatment plan modeling module which is adapted to receive all of the input data and develop a treatment plan optimization model. Employing a true global optimization approach, the treatment plan optimization model incorporates all of the physical and clinical variables related to the external beam delivery unit and the target volume that define the global system. The systems also have a global optimization module which is adapted to determine an optimal treatment plan based on the treatment plan optimization model and all the input data. The systems may also include a visual evaluation functionality which is adapted to display information related to the optimal treatment plan to a physician.

The present invention can also be viewed as providing methods for providing an optimal treatment plan for delivering a prescribed radiation dose to a predefined target volume within a patient using an external beam radiation delivery unit. Briefly, one such method involves (1) receiving information related to the prescribed radiation dose, the predefined target volume, and parameters associated with the external beam delivery unit, (2) developing a treatment plan optimization model based on a plurality of variables corresponding to the information, and (3) outputting an optimal treatment plan based on the treatment plan optimization model and the information.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The systems and methods according to the present invention can be better understood with reference to the following drawings.

DETAILED DESCRIPTION OF THE INVENTION

Figure 1:
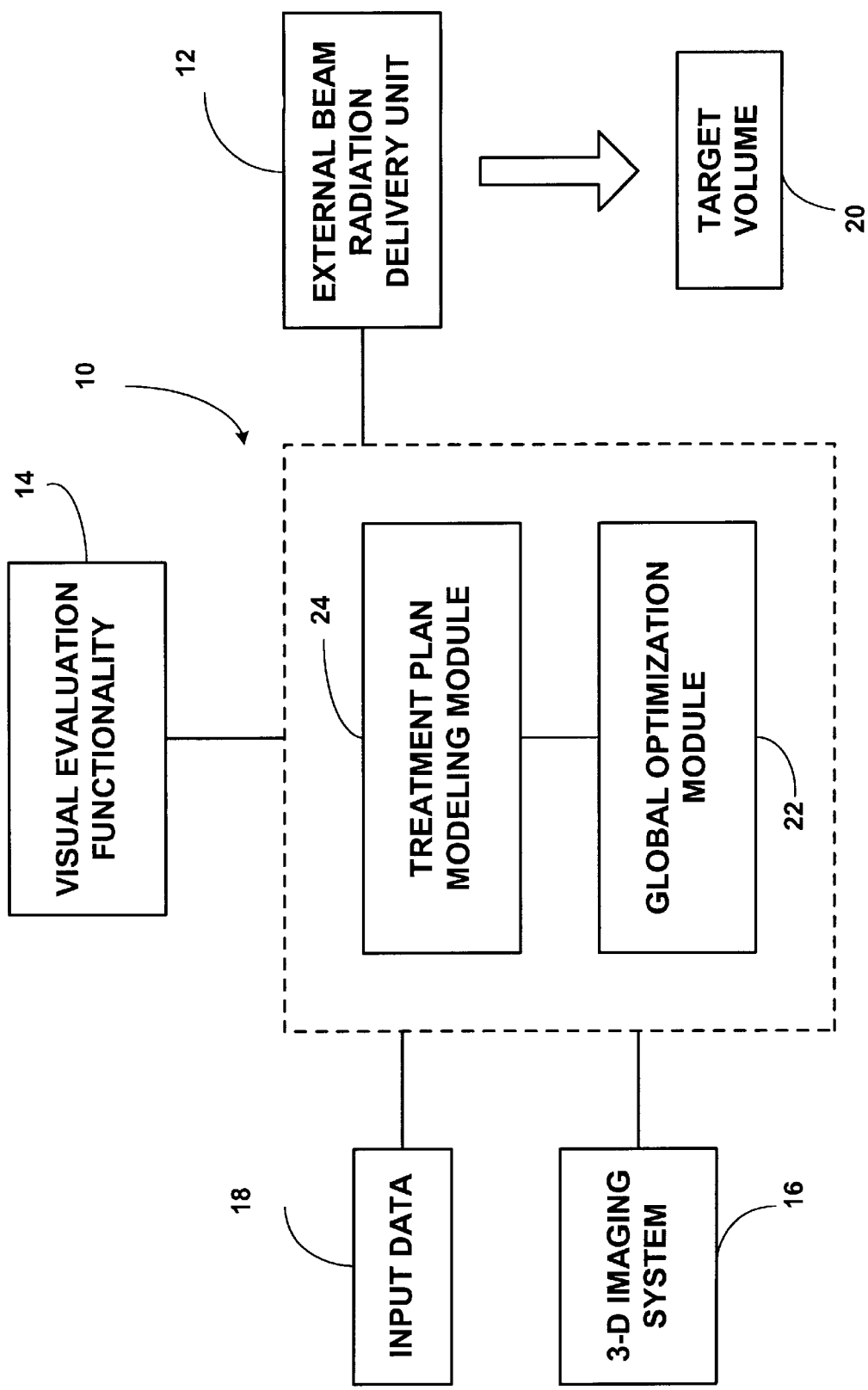
FIG. 1 is a functional block diagram of one embodiment of a system according to the present invention.

Having summarized the invention above, reference is now made in detail to the description of the invention as illustrated in the drawings. While the invention will be described in connection with these drawings, there is no intent to limit it to the embodiment or embodiments disclosed. On the contrary, the intent is to cover all alternatives, modifications and equivalents included within the spirit and scope of the invention as defined by the appended claims.

System Overview

FIG. 1 illustrates a functional block diagram of a preferred embodiment of a system 10 according to the present invention for enabling global optimization of treatment planning for external beam radiation therapy. System 10 is connected to an external beam delivery unit 12, visual evaluation functionality 14, and three-dimensional imaging system 16.

External beam delivery unit 12 may be any conventional equipment used in external beam radiation therapy for delivering doses of radiation to a target volume 20 within a patient, such as, for example, a linear accelerator (LINAC), a Gamma Knife, or any other external device capable of providing a radiation source. External beam delivery unit 12 may comprise a plurality of external beams having variable intensity, a plurality of collimators for adjusting the size of the beams, and a mechanism for moving the unit with respect to a patient positioned within a stereotactic frame in order to adjust the angle and entry point of each radiation beam.

System 10 also contemplates using various radiation modalities with external beam delivery unit 12. For example, system 10 may be used with static conformal radiation therapy (SCRT), non-coplanar arc stereotactic radiosurgery (NASR), intensity modulated radiation therapy (IMRT), and intensity modulated arc therapy (IMAT).

SCRT involves the use of three-dimensional computer planning systems to geometrically shape the radiation field to ensure adequate coverage of the target, while sparing normal tissue. The tools for SCRT include patient-specific CT data, beam's-eye-view (BEV) treatment planning, and multileaf collimators (MLC). Guided by the target contours identified in the CT images, beam orientations are chosen and beam apertures are accurately delineated using BEV. The beam aperture can be fabricated with conventional blocks or defined by MLC. The dose distribution within the field is determined by choice of beam intensity and simple modulators such as wedges and tissue compensators.

NASR is a technique used for treating brain tumors. Radiosurgery is distinguished from conventional external beam radiation therapy of the central nervous system by its localization and treatment strategy. In radiosurgery, the target volume of tissue is much smaller (tumors 10–35 mm in diameter), the number of fractions (treatment sessions) is much less, and the dose per fraction is much larger than in conventional radiotherapy. Radiosurgery involves the use of external beams of radiation guided to a desired point within the brain using a precisely calibrated stereotactic frame mechanically fixed to the head, a beam delivery unit, such as a LINAC Gamma Knife, and three-dimensional medical imaging technology. For LINAC radiosurgery, the table on which the patient lies and the beam delivery unit are capable of rotating about distinct axes in order to adjust the angle and entry point of a radiation beam. The tissue affected by each beam is determined by the patient's position within the stereotactic frame, by the relative position of the frame in relation to the beam delivery unit, by collimators that adjust the size of the beam, and by the patient's anatomy. Additionally, the intensity of each beam can be adjusted to govern its dose contribution to each point.

IMRT is a recently developed treatment modality in radiotherapy. In IMRT the beam intensity is varied across the treatment field. Rather than being treated with a single, large, uniform beam, the patient is treated instead with many very small beams, each of which can have a different intensity. When the tumor is not well separated from the surrounding organs at risk—such as what occurs when a tumor wraps itself around an organ—there may be no combination of uniform intensity beams that will safely separate the tumor from the healthy organ. In such instances, adding intensity modulation allows more intense treatment of the tumor, while limiting the radiation dose to adjacent healthy tissue.

IMAT is a form of IMRT that involves gantry rotation and dynamic multileaf collimation. Non-coplanar or coplanar arc paths are chosen to treat the target volume delineated from CT images. The arcs are chosen such that intersecting a critical structure is avoided. The fluence profiles at every 5 degrees are similar to a static IMRT field. As the gantry rotates, the dynamic MLC modulates the intensity to deliver the dose to the target volume while sparing normal tissue. The large number of rotating beams may allow for a more conformal dose distribution than the approach of multiple intensity modulated beams.

Thus, the systems and methods of the present invention are not limited to a particular type of external beam delivery unit 12 or a particular modality, but instead may employ any type of external beam delivery unit or radiation modality.

Visual evaluation functionality 14 may be any conventional imaging module adapted to interface with system 10 and capable of visually displaying an optimal treatment plan for delivering radiation to a patient using external beam delivery unit 12. Visual evaluation functionality 14 may be a computer monitor, a television monitor, any type of printout from a computer, or any other imaging module used by physicians to evaluate the effectiveness of a particular treatment plan for a patient. For example, visual evaluation functionality 14 may be configured to enable physicians to view dose-volume histograms and isodose surfaces for a treatment plan overlayed with a diagram of the target volume and surrounding areas, including normal surrounding tissue and critical structures.

Three-dimensional imaging system 16 may be any three-dimensional imaging technology used to delineate target volume 20 of a tumor or similar region within a patient, such as, for example, a computed tomography (CT) system, a magnetic resonance imaging (MRI) system, or any similar system. It should be understood by skilled persons in the art that there are many ways to capture images of lesions within a human body, and, therefore, this invention should not be limited to any particular type of imaging system. The important aspect is that imaging system 16 is capable of identifying the contours of target volume 20 along with surrounding normal tissues and critical structures.

Figure 2:
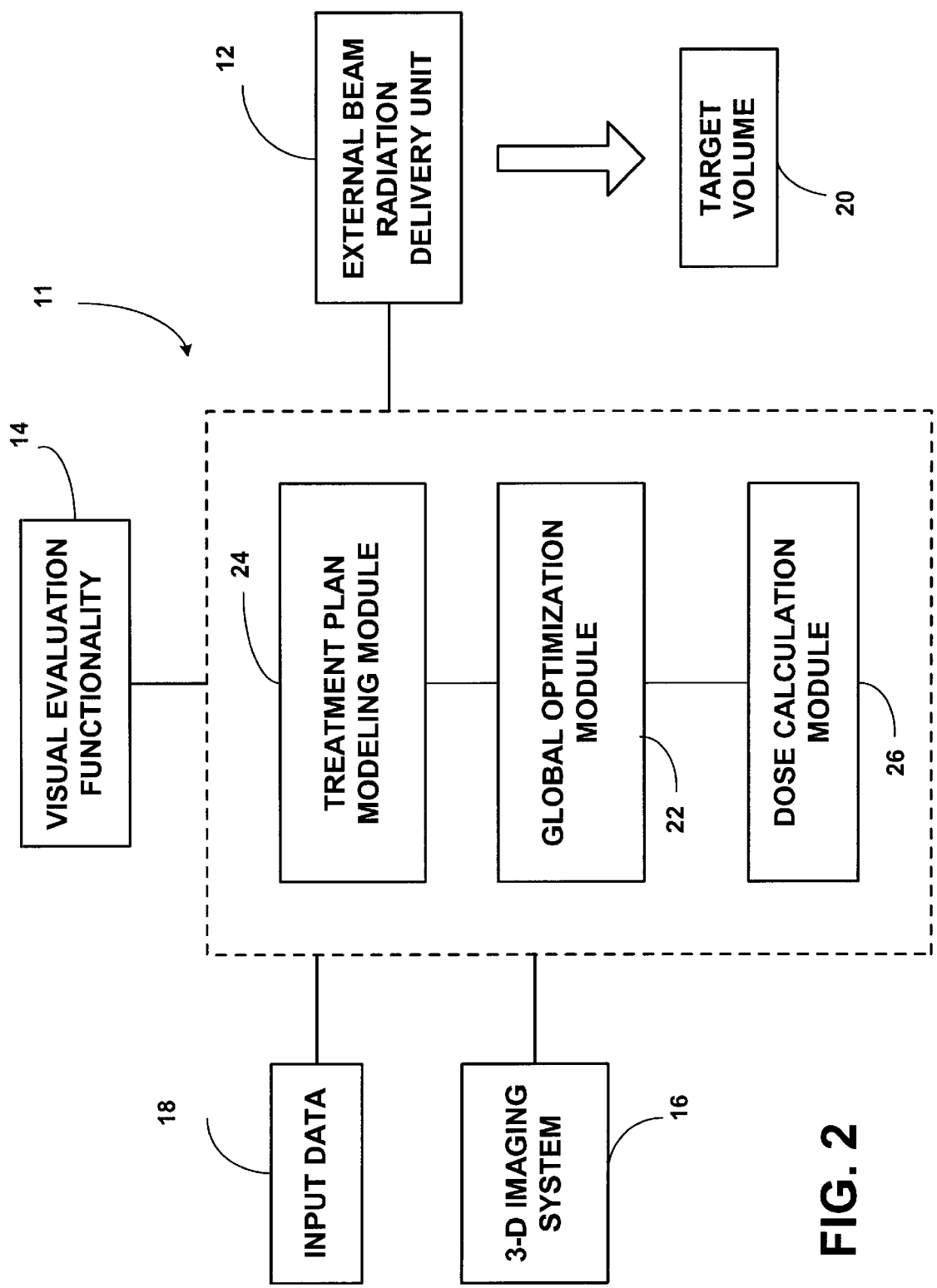
FIG. 2 is a functional block diagram of another embodiment of a system according to the present invention.

As shown in FIG. 1, system 10 comprises two main components: global optimization module 22 and treatment plan modeling module 24. FIG. 2 shows an alternative embodiment of a system 11 according to the present invention. System 11 is similar to system 10 except that it incorporates a third component, dose calculation module 26. Each of these components will be described in detail below.

System Input

Referring again to FIG. 1, system 10 receives various inputs from imaging system 16, as well as input data 18. Although in the preferred embodiment input data 18 represents all information input into system 10 not received from imaging system 16, it should be noted that input data 18 may actually come from any source. For example, input data 18 may be received by system 10 as a manual input by a physician or automatic input via a computer directed by a physician. FIG. 1 is merely illustrating by way of example that system 10 receives information related to target volume 20 via imaging system 16 and that all other input is referred to as input data 18.

Input data 18 to system 10 includes CT and/or MRI images of target volume 20. The contours of target volume 20 and surrounding normal tissue and critical structures are identified and segmented using the medical images. These anatomical contours are used as inputs to system 10. Other inputs include clinical planning information such as prescription dose; target lower and upper bounds on the radiation dose delivered to the tumor volume, nearby healthy tissue, and critical structures; choice of possible isocenters; and desired number of beams, isocenters, and couch angles used in the final physical plan. The anatomical contours and dose calculation points from the imaging coordinate systems are transformed via a coordinate system transformation algorithm to the stereotactic coordinate system. An automated arc selection method employing computational geometry techniques is used to select a representative collection of candidate arcs.

As described above, system 10 is not limited to a particular type of apparatus for external beam delivery unit 12 or a particular modality. Nonetheless, for exemplary purposes, system 10 will be described with respect to a preferred method using LINAC arcing radiosurgery.

In LINAC arcing radiosurgery, the following treatment parameters define an arc: a target point location variable t; collimator size C, gantry initial and end angles $\theta_i$; and $\theta_e$ and couch angle $\theta$. The isocenters for candidate arcs are chosen in 2 mm intervals and reside in the target volume. The candidate arcs vary the couch and gantry angles in 1° increments from −90° to 90° and 0° to 359°, respectively. These candidate beam orientation parameters (couch and gantry angles) are selected so that they match the beam orientations selected by clinicians manually. Twelve circular collimator sizes are applied to the candidate arcs, ranging from 12.5 to 40 mm in 2.5 mm steps. The resulting collection of beams comprise a large set of candidate beams used for instantiating a treatment plan optimization model used by treatment plan modeling processor 24.

Treatment Plan Optimization Model/Treatment Plan Modeling Module

As shown in FIG. 1 and mentioned above, system 10 comprises treatment plan modeling module 24 and global optimization module 22. Treatment plan modeling module 24 receives inputs 18, and based on these inputs, creates a treatment plan optimization model. The treatment plan optimization model incorporates every potential variable included within input 18. In other words, the treatment plan optimization model represents a global optimization of every potential variable within the system. As will be described in detail below, upon completion, treatment plan modeling module 24 provides the resulting treatment plan optimization model to global optimization module 22 where an optimal treatment plan is determined based on inputs 18.

A preferred embodiment of a treatment plan optimization model will now be described. Given a collection of selected arcs indexed as $\{1, \ldots, N_A\}$, comprised of target points $\{1, \ldots, N_t\}$ and couch angles $\{1, \ldots, N_\phi\}$ (note that each arc associates with a specified collimator size, gantry initial and end angles, target position, and couch angle), the preferred treatment plan optimization model incorporates non-negative continuous variables to record the intensity used for each arc. If an arc is used, thus indicating that the intensity is greater than zero, then it contributes a certain amount of radiation dosage to each voxel in target volume 20. Thus, once the set of potential arc intensities is specified, the total radiation dose received at each voxel can be modeled. For example, in the preferred treatment plan optimization model, $w_a \geq 0$ denotes the intensity (weight) of arc a. Then the total radiation dose at a voxel P is given by the following expression:

$$\sum_{a=1}^{N_A} D_{P,a} w_a \quad \text{Equation 1}$$

where $D_{P,a}$ denotes the dose contribution to voxel P from arc a as given by the following expression:

$$D_{P,a} = S(C) \int_{\theta_i}^{\theta_e} TMR(\theta, \phi_a, \bar{d}_{P,a}, r_{P,a}, C_P)$$

$$OAR(\theta, \phi_a, \bar{d}_{P,a}, r_{P,a}, C_P) IVSQ(\theta, \phi_a, \bar{d}_{P,a}, r_{P,a}) d\theta \quad \text{Equation 2}$$

$D_{P,a}$ may be calculated using standard dose calculation tools and merely included with input data 18. As shown in FIG. 2, an alternative embodiment of a system 11 may employ an internal dose calculation module 26 to perform this calculation. Dose calculation module 26 may employ computational geometry and measured dosimetry parameters in a semi-empirical formulation to calculate $D_{P,a}$. For instance, to calculate the dose from a fixed beam, say at a point P in the brain, a ray is formed joining P and a point on the central axis of the radiation beam. Dose calculation module 26 may employ a computation method which uses measured dosimetry parameters obtained from a water phantom. The parameters may include: tissue maximum ratios (TMR), total scatter correction factors (S), inverse square correction (IVSQ), and off-axis ratio (OAR). The depth, d, of tissue penetrated by the central ray of the radiation beam, and the depth, $\bar{d}$, of tissue penetrated by the ray formed by connecting the dose calculation voxel P to the radiation source are computed by a ray tracing method. The distance, r, from the dose calculation voxel to the central ray is also computed. Using the values d, $\bar{d}$, and r, the measured dosimetry parameters are calculated for the point P. The dose per monitor unit deposited by one arc of the gantry is the sum of a set of static beams which approximate this arc. The total dose deposited to a point ($D_{P,a}$) is the summation of the dose over all arcs.

The preferred embodiment of the treatment plan optimization model may also incorporate a variety of desirable constraints. For example, clinically prescribed lower and upper bounds, say $L_P$ and $U_P$, for the radiation dose at voxel P can be incorporated with Equation 1 to form the following dosimetric constraints:

$$\sum_{a=1}^{N_A} D_{P,a} w_a \geq L_P \text{ and } \sum_{a=1}^{N_A} D_{P,a} w_a \leq U_P \quad \text{Equation 3}$$

Note that a is characterized by the target point, couch angles, collimator size, and gantry initial and end angles. Thus, a could be more accurately referred to as $a_{t,C,\theta_i,\theta_e,\phi}$. However, for brevity of notation, subscripts are listed only as needed to enhance clarity.

The preferred embodiment of the treatment plan optimization model may also constrain the characteristics of beam arrangements from external beam delivery unit 12. To control the number of target points specified by the optimal plan, the treatment plan optimization model defines a 0/1 indicator variable $t_j$ to denote if target point j is used or not. The following constraints capture the use of target point j in the resulting plan when an arc with target point j is used.

$$w_{a_j} \leq M_{a_j} t_j \text{ and } \sum_{j=1}^{N_t} t_j \leq T \quad \text{Equation 4}$$

Here, $M_{a_j}$ is a positive constant and can be selected as the largest possible beam intensity among candidate arcs having target point j. The second constraint can then be imposed, where T is the maximum number of target points acceptable by the physician for the particular patient. Although complications from radiosurgery treatments may increase with the number of isocenters, it has been shown that for highly irregular shaped tumor volumes, multiple isocenters may improve the conformity of the high dose region. With current state of the art methods, determining an "optimal" beam configuration with multiple target points is extremely difficult and time consuming. The systems and methods of the present invention enable clinicians to include such constraints within the model to assist in determining an optimal treatment plan.

The preferred embodiment of the treatment plan optimization model may also constrain the number of couch angles, and the number of arcs used in the resulting plan due to the physical requirement of adjusting the equipment to achieve the desired configurations for each round of irradiation. For example, the treatment plan optimization model, may employ 0/1 integer variable $\phi_j$, to model the use of couch angle j, and 0/1 integer variable $\beta_a$ to model the use of arc a. In this manner, when $w_{a_j}$ ($w_a$) is positive, then $\phi_j$ ($\beta_a$) will be set to 1. These constraints may take the following form:

$$w_{a_j} \leq N_{a_j} \phi_j \text{ and } \sum_{j=1}^{N_\phi} \phi_j \leq \Phi \quad \text{Equation 5}$$

$$w_a \leq R_a \text{ and } \sum_{a=1}^{N_a} b_a \leq B \quad \text{Equation 6}$$

where $N_{a_j}$ and $R_a$ are constants and can be chosen as the largest possible intensity emitted from arc a, respectively, and $\Phi$ ( and B are the maximum number of couch angles allowed and beam configurations desired in the optimal plan, respectively.

In a similar manner, the treatment plan optimization model may also constrain the collimator size and the number of distinct gantry angles used in the resulting plans. In addition, it may also impose a minimum beam intensity for each arc to ensure that the resulting plan is practical. These constraints may be important if, in absence of such restrictions, the optimization system returns plans involving, say, hundreds of distinct configurations. Too many configurations may be physically difficult to manage, and it will be impractical to deliver a very complex plan. The treatment plan optimization model is configured to enable dose calculation module 26 to return a realistic plan which can be carried out in a reasonably easy fashion in the treatment delivery room.

The treatment plan optimization model may also incorporate additional constraints to enforce clinical properties desired for individual patients. A variety of optimization objectives can be incorporated with these constraints to direct the selection of a treatment plan. For example, one possible approach is to find a maximal feasible subsystem among the dosimetric constraints. Clinically, this translates into finding a beam configuration which gives the maximum percentage of tumor volume, critical structure and normal tissue satisfying their respective target dose levels. Due to the proximity of critical structures and the tumor volume, it is not possible to find a beam geometry and intensity which satisfies all the dosimetric constraints given in Equation 3. In this case, the treatment plan optimization model may include an indicator variable incorporated into each constraint to capture whether or not the desired dose bound is achieved.

Alternatively, the treatment plan optimization model may be configured to seek a treatment plan which results in the minimum deviation from the clinical prescription bounds. In this case, continuous variables can be added to the constraints in Equation 3 to measure the deviations from the lower and upper bound for each voxel P.

In the preferred embodiment of the systems and methods of the present invention, the treatment plan optimization model employs a mixed integer programming approach to determine an optimal treatment plan which guarantees 100% coverage to tumor volume while minimizing the dose received by proximal critical structures and/or normal tissue. In particular, instead of providing upper and lower dose bounds, the clinician inputs the desired prescription dose received by the tumor volume. In this embodiment, the treatment plan optimization model formulates the problem as: Minimize $$\sum_{P \in PTV} f_P$$

Subject to the constraints $$\sum_{a=1}^{N_A} D_{P,a} w_a - f_P = PRDOSE \quad P \in PTV \quad \text{Equation 7}$$

$$w_{a_j} \leq M_{a_j} t_j \quad a_j \in \{1, \ldots, N_A\}, j \in \{1, \ldots, N_t\}$$

$$\sum_{j=1}^{N_t} t_j \leq T$$

$$w_{a_j} \leq N_{a_j} \phi_j \quad a_j \in \{1, \ldots, N_A\}, j \in \{1, \ldots, N_\phi\}$$

$$\sum_{j=1}^{N_\phi} \phi_j \leq \Phi$$

$$w_a \leq R_a b_a \quad a \in \{1, \ldots, N_A\}$$

$$\sum_{a=1}^{N_A} b_a \leq B$$

$$w_a, f_P \geq 0; t_j, \phi_j, b_a \in \{0, 1\}$$

In Equation 7, PRDOSE is the clinical prescription dose for the predefined tumor volume PTV, T is the maximum number of target points desired by the physicians for the particular patient, and $\Phi$ and B are the maximum number of couch angles allowed and beam configurations desired in the optimal plan, respectively. As described above, $M_{a_j}$, $N_{a_j}$, and $R_a$ are positive constants and can be chosen as the largest intensity possible emitted from a single arc. In Equation 7, the variable $f_P$ denotes the amount of irradiation exceeding the prescription dose at point P. Since $f_P$ is nonnegative, the dose calculation model ensures that point P will receive at least the prescription dose. For points P on the tumor surface, which separates the tumor volume from the normal tissue, in addition to measuring the excess radiation to the tumor surface, $f_P$ can also be viewed as a measure of radiation to the immediately surrounding normal tissue. Minimizing the sum of the variables $f_P$ has the effect of providing a uniform dose distribution on the tumor volume while producing a steep dose gradient outside of the tumor volume. Thus, even in the absence of a critical structure constraining the treatment plan, the dose calculation model ensures that proximal normal tissues receive minimal dose due to rapid dose fall-off.

Global Optimization Module

Global optimization module 22 receives the treatment plan optimization model from treatment plan modeling module 24 and input 18. Based on this information, global optimization module 22 solves instances of the treatment plan optimization model. In the preferred embodiment, a classical branch-and-bound approach is used to determine a true global optimal solution. Moreover, the "intelligent" search mechanism of the branch-and-bound method enables large sections of the solution space to be eliminated from consideration—knowing that no solution within can be optimal—without actually examining each solution within.

The branch-and-bound is a tree search approach where, at each node of the tree, certain binary variables are fixed to zero or one, and the remaining binary variables are relaxed (i.e., allowed to assume any value between zero and one). This results in a linear program (LP) being associated with each node of the tree. The LP at the root node is simply the original 0/1 mixed integer programming (MIP) instance. with all of the binary variables relaxed. The tree is constructed such that the binary variables fixed in a parent node will be fixed identically in any of its children, and each child will have an additional binary variable fixed to zero or one. Typically, children are formed in pairs as follows. Assume that the LP at a given node is solved, and one or more of the relaxed binary variables is fractional in the optimal solution. One selects such a fractional binary variable and branches on it. In other words, two child nodes are formed; one with the selected binary variable fixed to zero, and the other with the selected binary variable fixed to one. Of course, each child also inherits all of the fixed binary variables of its parent. Note that the objective value of a child node can be no smaller (in the case of minimization) than the objective value of its parent.

If the linear program at a given node is solved and the optimal solution happens to have integral values for all the relaxed binary variables, then this solution is feasible for the original 0/1 mixed integer program. Once a feasible solution for the original problem is found, the associated objective value can be used as an upper bound (in the case of minimization) for the objective values of LP's at other nodes. In particular, if an LP at another node is solved, and its objective value is greater than or equal to the upper bound, then none of its children could yield a feasible solution for the original MIP with a smaller objective value than the one already obtained. Hence, no further exploration of this other node is needed, and the node is said to be fathomed.

Two other criteria for fathoming a node are apparent: if the associated LP is infeasible, or if the optimal solution of the LP has integral values for all relaxed binary variables, then no further exploration of the node is required. In the latter case, the optimal objective value of the LP will be compared with the current upper bound, and the upper bound will be updated if needed. The tree search ends when all nodes are fathomed. Although a variety of strategies may be used for intelligently selecting branching variables and nodes to process, in the preferred embodiment, the branch-and-bound is coupled with other computational devices, such as problem preprocessing, primal heuristics, global and local reduced-cost fixing, and cutting planes.

In the preferred embodiment, global optimization module is based on a branch-and-bound MIP solver that is built on top of general-purpose mixed integer research code (MIPSOL). The general purpose code, which incorporates all of the above mentioned computational devices, has been shown to be effective in solving a wide variety of large-scale real-world MIP instances.

System Implementation

Figure 3:
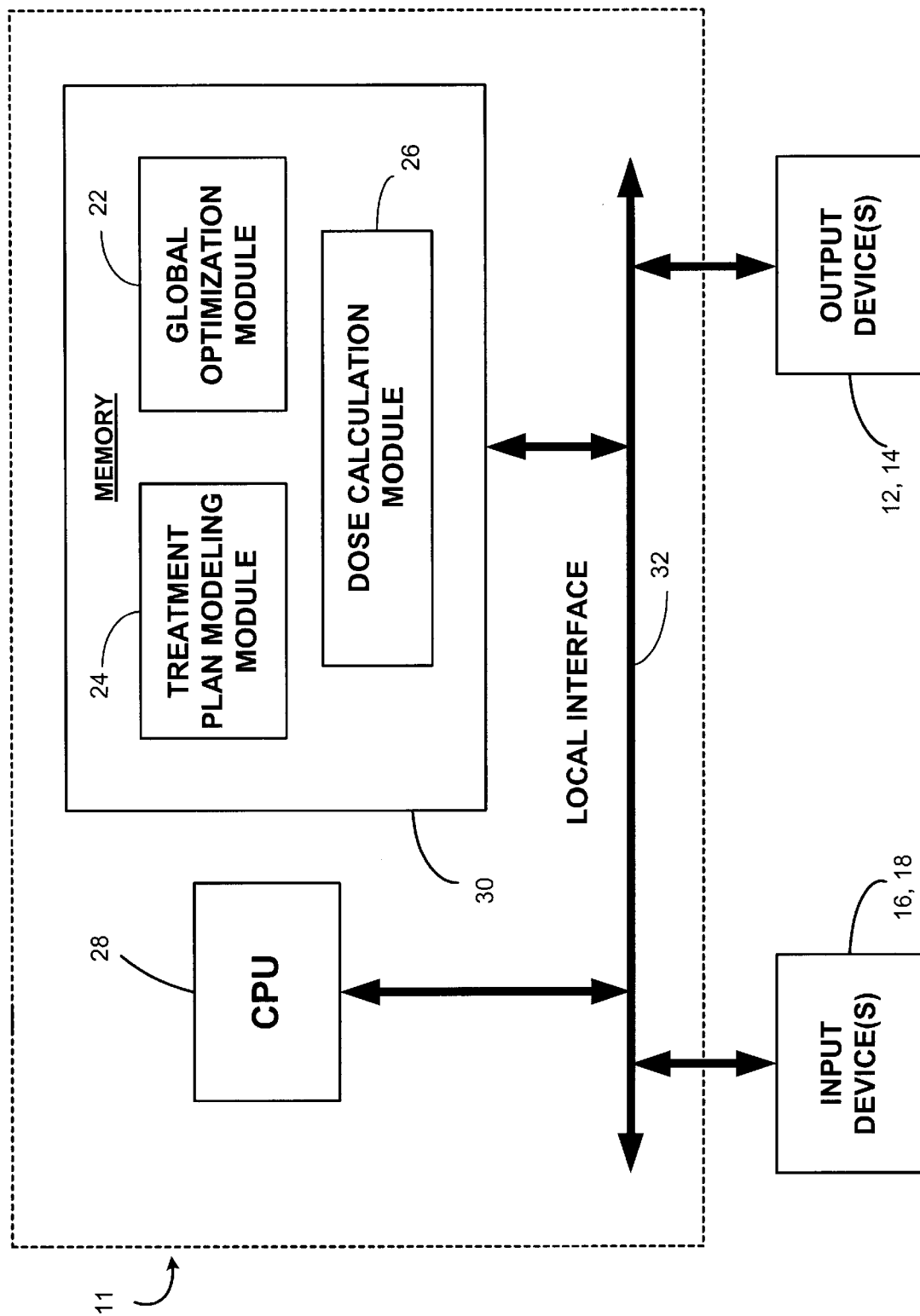
FIG. 3 is a block diagram of a preferred implementation of the system illustrated in FIG. 2.

System 10 of FIG. 1 and system 11 of FIG. 2 can be implemented in hardware, software, firmware, or a combination thereof. FIG. 3 illustrates a preferred implementation of system 11. As described above, system 11 is similar to system 10 except for the inclusion of dose calculation module 26. Thus, although the preferred implementation is described below, system 10 is implemented in a similar fashion.

As shown in FIG. 3, system 11 comprises computer processing unit (CPU) 28, memory 30, and local interface 32. System 11 may communicate via local interface 32 with input devices 34 and output devices 36. As shown in FIG. 2, input devices 34 may include three-dimensional imaging system 16 and/or input data 18 and output devices 36 may include external beam delivery unit 12 and/or visual evaluation functionality 14.

Treatment plan modeling module 24, global optimization module 22, and dose calculation module 26 are implemented software or firmware that is stored in memory 30 and executed by CPU 28. CPU 28 may be any suitable instruction execution system. It should be understood by persons skilled in the art that treatment plan modeling module 24, global optimization module 22, and dose calculation module 26 may also implemented in hardware. For example, in accordance with the systems and methods of the present invention, treatment plan modeling module 24, global optimization module 22, and dose calculation module 26 may be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 4:
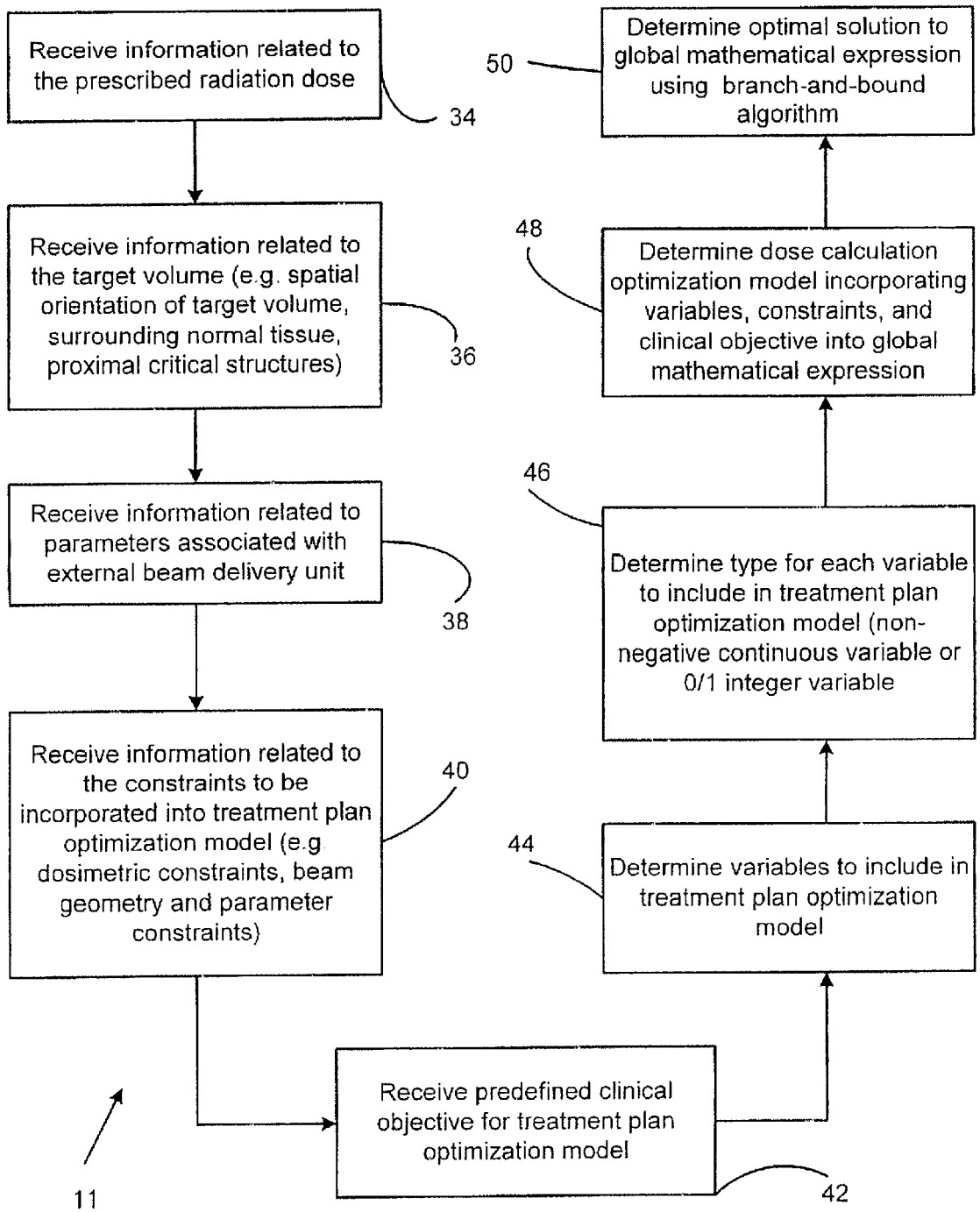
FIG. 4 is a flowchart illustrating the functionality and operation of the system illustrated in FIGS. 2 and 3.

The flowchart of FIG. 4 shows the functionality and operation of one implementation of system 11. Any process descriptions or blocks in flowcharts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

Referring to FIG. 4, at 34, information related to the prescribed dose is received. At 36, information related to target volume 20 is received. As described above, this information may include CT and/or MRI images identifying the contours of target volume 20 and surrounding normal tissue and critical structures. Information related to external beam delivery unit 12, such as beam geometry and beam parameters, is received at 38. At 40, information related to the constraints to be incorporated into the treatment plan optimization model is received. For example, the treatment plan optimization model may incorporate dosimetric constraints and constraints on various characteristics of the beam arrangements. At 42, predefined clinical objectives are received. At 44, the variables to include in the treatment plan optimization model are determined. As described above, the present invention employs a global approach, and thus, all possible variables are included in the treatment plan optimization model. At 46, the type of variable for each variable is determined, for example, whether the variable will be represented in the treatment plan optimization model as a non-negative continuous variable or a 0/1 integer variable. At 48, the treatment plan optimization model is determined by incorporating the variables, constraints, and the clinical objective into a global mathematical expression. At 50, a branch-and-bound algorithm is used to determine the optimal treatment plan.

Treatment plan modeling module 24, global optimization module 22, and dose calculation module 26, which comprise an ordered listing of executable instructions for implementing logical functions, can be embodied in any computer-readable medium for use by or in connection with CPU 28 or any other instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A method of providing an optimal treatment plan for delivering a prescribed radiation dose to a predefined target volume within a patient using an external beam radiation delivery unit, comprising:
   a. receiving information related to (1) the prescribed radiation dose, (2) the predefined target volume, and (3) a plurality of parameters associated with the external beam delivery unit;
   b. developing a treatment plan optimization model based on a plurality of variables corresponding to the information which define a global system; and
   c. producing an optimal treatment plan based on the treatment plan optimization model and the information.

2. The method of claim 1, wherein at least one of the plurality of variables corresponding to the information is a 0/1 indicator variable.

3. The method of claim 2, wherein developing a treatment plan optimization model involves constraining at least one of the plurality of variables corresponding to the information within a predefined limit.

4. The method of claim 3, wherein outputting the optimal treatment plan is further based on a predefined clinical objective.

5. The method of claim 1, further comprising implementing the optimal treatment plan on the patient using the external beam delivery unit.

6. A method of providing an optimal treatment plan for delivering a prescribed radiation dose to a predefined target volume within a patient using an external beam radiation delivery unit, comprising:
   a. receiving information related to (1) the prescribed radiation dose, (2) the predefined target volume, and (3) a plurality of parameters associated with the external beam delivery unit;
   b. developing a treatment plan optimization model based on a plurality of 0/1 indicator variables corresponding to the information which define a global system and which involves constraining at least one of the plurality of 0/1 indicator variables corresponding to the information within a predefined limit; and
   c. producing an optimal treatment plan based on the treatment plan optimization model, the information, and a predefined clinical objective;

wherein the external beam delivery unit is a linear accelerator used in arcing radiosurgery and the plurality of 0/1 indicator variables corresponding to the information include (1) a target point location variable t, (2) a collimator size variable C, (3) a gantry initial angle variable $\theta_i$, (4) a gantry end angle variable $\theta_e$, (5) a couch angle variable $\phi$, (6) a predefined target volume point variable P, and (7) an arc variable a being a function of t, C, $\theta_i$, $\theta_e$, $\phi$ and the predefined clinical objective comprises the expression:

Minimize $$\sum_{P \in PTV} f_P$$

Subject to the constraints $$\sum_{a=1}^{N_A} D_{P,a} w_a - f_P = PRDOSE \quad P \in PTV$$

$$w_{a_j} \leq M_{a_j} t_j \quad a_j \in \{1, \ldots, N_A\}, j \in \{1, \ldots, N_t\}$$

$$\sum_{j=1}^{N_t} t_j \leq T$$

$$w_{a_j} \leq N_{a_j} \phi_j \quad a_j \in \{1, \ldots, N_A\}, j \in \{1, \ldots, N_\phi\}$$

$$\sum_{j=1}^{N_\phi} \phi_j \leq \Phi$$

$$w_a \leq R_a b_a \quad a \in \{1, \ldots, N_A\}$$

$$\sum_{a=1}^{N_A} b_a \leq B$$

$$w_a, f_P \geq 0; t_j, \phi_j, b_a \in \{0, 1\}$$

wherein PRDOSE corresponds to the prescribed radiation dose for the predefined target volume PTV, T corresponds to a total number of target points in the predefined target volume, Φ corresponds to a predefined maximum number of couch angles permitted in the optimal treatment, B corresponds to a predefined maximum number of beam configurations permitted in the optimal treatment plan, $M_{a_j}$, $N_{a_j}$, and $R_a$ corresponds to predefined positive constants representing the largest possible intensity emitted from an arc, $f_P$ corresponds to an amount of radiation exceeding the prescription dose at P, and $\omega_a$ corresponds to the intensity of an arc a, $D_{P,a}$ corresponds to a total dose deposited to P over all arcs, $L_P$ corresponds to a predefined lower bound for a radiation dose at P, and $U_P$ corresponds to a predefined upper bound for a radiation dose at P.

7. The method of claim 6, further comprising providing the optimal treatment plan to a visual evaluation system where information related to the optimal treatment plan may be displayed.

8. A system for providing an optimal treatment plan for delivering a prescribed radiation dose to a predefined target volume within a patient using an external beam delivery unit, comprising:
   a. a means for receiving information related to (1) the prescribed radiation dose, (2) the predefined target volume, and (3) a plurality of parameters associated with the external beam delivery unit;
   b. a means for developing a treatment plan optimization model based on a plurality of variables corresponding to the information which define a global system; and
   c. a means for determining an optimal treatment plan based on the treatment plan optimization model and the information.

9. The system of claim 8, wherein at least one of the plurality of variables corresponding to the information is a 0/1 indicator variable.

10. The system of claim 9, wherein the treatment plan optimization model contains constraints on at least one of the plurality of variables corresponding to the information within a predefined limit.

11. The system of claim 10, wherein the means for determining an optimal treatment plan is further adapted to incorporate a predefined clinical objective.

12. The system of claim 8, further comprising a means for implementing the optimal treatment plans on the patient.

13. A system for providing an optimal treatment plan for delivering a prescribed radiation dose to a predefined target volume within a patient using an external beam delivery unit, comprising:
   a. a means for receiving information related to (1) the prescribed radiation dose, (2) the predefined target volume, and (3) a plurality of parameters associated with the external beam delivery unit;
   b. a means for developing a treatment plan optimization model based on a plurality of 0/1 indicator variables corresponding to the information which define a global system and which involves constraining at least one of the plurality of 0/1 indicator variables corresponding to the information within a predefined limit; and
   c. a means for producing an optimal treatment plan based on the treatment plan optimization model, the information and a predefined clinical objective;
   wherein the external beam delivery unit is a linear accelerator used in arcing radiosurgery and the plurality of variables corresponding to the information include (1) a target point location variable t, (2) a collimator size variable C, (3) a gantry initial angle variable $\theta_i$, (4) a gantry end angle variable $\theta_e$, (5) a couch angle variable $\phi$, (6) a predefined target volume point variable P, and (7) an arc variable a being a function of t, C, $\theta_i$, $\theta_e$, $\phi$ and the predefined clinical objective comprises the expression:

Minimize $$\sum_{P \in PTV} f_P$$

Subject to the constraints $$\sum_{a=1}^{N_A} D_{P,a} w_a - f_P = PRDOSE \quad P \in PTV$$

$$w_{a_j} \leq M_{a_j} t_j \quad a_j \in \{1, \ldots, N_A\}, j \in \{1, \ldots, N_t\}$$

$$\sum_{j=1}^{N_t} t_j \leq T$$

$$w_{a_j} \leq N_{a_j} \phi_j \quad a_j \in \{1, \ldots, N_A\}, j \in \{1, \ldots, N_\phi\}$$

$$\sum_{j=1}^{N_\phi} \phi_j \leq \Phi$$

$$w_a \leq R_a b_a \quad a \in \{1, \ldots, N_A\}$$

$$\sum_{a=1}^{N_A} b_a \leq B$$

$$w_a, f_P \geq 0; \, t_j, \phi_j, b_a \in \{0,1\}$$

wherein PRDOSE corresponds to the prescribed radiation dose for the predefined target volume PTV, T corresponds to a total number of target points in the predefined target volume, Φ corresponds to a predefined maximum number of couch angles permitted in the optimal treatment, B corresponds to a predefined maximum number of beam configurations permitted in the optimal treatment plan, $M_{a_j}$, $N_{a_j}$, and $R_a$ corresponds to predefined positive constants representing the largest possible intensity emitted from an arc, $f_P$ corresponds to an amount of radiation exceeding the prescription dose at P, and $\omega_a$ corresponds to the intensity of an arc a, $D_{P,a}$ corresponds to a total dose deposited to P over all arcs, $L_P$ corresponds to a predefined lower bound for a radiation dose at P, and $U_P$ corresponds to a predefined upper bound for a radiation dose at P.

14. The system of claim 13, further comprising a means for visually evaluating the optimal treatment plan.

15. A system for providing an optimal treatment plan for delivering a prescribed radiation dose to a predefined target volume within a patient using an external beam radiation delivery unit, comprising:
   a. an interface which is adapted to receive information related to (1) the prescribed radiation dose, (2) the predefined target volume, and (3) a plurality of parameters associated with the external beam delivery unit;
   b. a treatment plan modeling module which is adapted to receive the information and develop a treatment plan optimization model containing a plurality of variables corresponding to the information which define a global system; and c. a global optimization module which is adapted to determine an optimal treatment plan based on the treatment plan optimization model and the information.

16. The system of claim 15, wherein at least one of the plurality of variables corresponding to the information is a 0/1 indicator variable.

17. The system of claim 16, wherein the treatment plan optimization model further contains constraints on at least one of the plurality of variables corresponding to the information within a predefined limit.

18. The system of claim 17, wherein the treatment plan optimization model incorporates a predefined clinical objective.

19. The system of claim 15, further comprising the external beam delivery unit which is adapted to implement the optimal treatment plan on the patient.

20. A computer-readable medium having a computer program for use by an external beam delivery unit having a plurality of parameters to determine an optimal treatment plan for delivering a prescribed radiation dose to a predefined target volume within a patient, the computer-readable medium comprising:

a. a first portion of code which receives information related to (1) the prescribed radiation dose, (2) the predefined target volume, and (3) a plurality of parameters associated with the external beam delivery unit and which develops a treatment plan optimization model based on a plurality of variables corresponding to the information which define a global system; and b. a second portion of code which receives the treatment plan optimization model and provides an optimal treatment plan.

21. The computer-readable medium of claim 20, wherein at least one of the plurality of variable corresponding to the information is a 0/1 indicator variable.

22. The computer-readable medium of claim 21, wherein the treatment plan optimization model constrains at least one of the plurality of variables corresponding to the information within a predefined limit.

23. The computer-readable medium of claim 22, wherein the treatment plan optimization model incorporates a predefined clinical objective.

24. A system for providing an optimal treatment plan for delivering a prescibed radiation dose to a predefined target volume within a patient using an external beam delivery unit, comprising:

a. an interface which is adapted to receive information related to (1) the prescribed radiation dose, (2) the predefined target volume, and (3) a plurality of parameters associated with the external beam delivery unit;

b. a treatment plan modeling module which is adapted to receive the information and develop a treatment plan optimization model containing a plurality of 0/1 indicator variables corresponding to the information which define a global system while constraining at least one of the plurality of 0/1 indicator variables corresponding to the information within a predefined limit; and c. a global optimization module which is adapted to determine an optimal treatment plan based on the treatment plan optimization model, the information, and a predefined clinical objective;

wherein the external beam delivery unit is a linear accelerator used in arcing radiosurgery and the plurality of variables corresponding to the information include (1) a target point location variable t, (2) a collimator size variable C, (3) a gantry initial angle variable $\theta_i$, (4) a gantry end angle variable $\theta_e$, (5) a couch angle variable $\phi$, (6) a predefined target volume point variable P, and (7) an arc variable a being a function of t, C, $\theta_i$, $\theta_e$, $\phi$ and the predefined clinical objective comprises the expression:

Minimize $$\sum_{P \in PTV} f_P$$

Subject to the constraints:

$$\sum_{a=1}^{N_A} D_{P,a} w_a - f_P = PRDOSE \quad P \in PTV$$

$$w_{a_j} \le M_{a_j} t_j \quad a_j \in \{1, \ldots, N_A\}, j \in \{1, \ldots, N_t\}$$

$$\sum_{j=1}^{N_t} t_j \le T$$

$$w_{a_j} \le N_{a_j} \phi_j \quad a_j \in \{1, \ldots, N_A\}, j \in \{1, \ldots, N_\phi\}$$

$$\sum_{j=1}^{N_\phi} \phi_j \le \Phi$$

$$w_a \le R_a b_a \quad a \in \{1, \ldots, N_A\}$$

$$\sum_{a=1}^{N_A} b_a \le B$$

$$w_a, f_P \ge 0; t_j, \phi_j, b_a \in \{0, 1\}$$

wherein PRDOSE corresponds to the prescribed radiation dose for the predefined target volume PTV, T corresponds to a total number of target points in the predefined target volume, $\Phi$ corresponds to a predefined maximum number of couch angles permitted in the optimal treatment, B corresponds to a predefined maximum number of beam configurations permitted in the optimal treatment plan, $M_{a_i}$, $N_{a_j}$, and $R_a$ corresponds to predefined positive constants representing the largest possible intensity emitted from an arc, $f_p$ corresponds to an amount of radiation exceeding the prescription dose at P, and $\omega_a$ corresponds to the intensity of an arc a, $D_{P,a}$ corresponds to a total dose deposited to P over all arcs, $L_P$ corresponds to a predefined lower bound for a radiation dose at P, and $U_P$ corresponds to a predefined upper bound for a radiation dose at P.

25. The system of claim 24, further comprising a visual evaluation functionally which is adapted to display information related to the optimal treatment plan.

26. The system of claim 25, further comprising the external beam delivery unit which is adapted to implement the optimal treatment plan on the patient.

27. A computer-readable medium having a computer program for use by an external beam delivery unit having a plurality of parameters to determine an optimal treatment plan for delivering a prescribed radiation dose to a predefined target volume within a patient, the computer-readable medium comprising:

a. a first portion of code which receives information related to (1) the prescribed radiation dose, (2) the predefined target volume, and (3) a plurality of parameters associated with the external beam delivery unit and which develops a treatment plan optimization model based on a plurality of 0/1 indicator variables corresponding to the information which define a global system; and b. a second portion of code which receives the treatment plan optimization model and provides a optimal treatment plan by constraining at least one of the plurality of 0/1 indicator variables within a predefined limit and which is based on a predefined clinical objective;

wherein the external beam delivery unit is a linear accelerator used in arcing radiosurgery and the plurality of 0/1 indicator variables corresponding to the information include (1) a target point location variable t, (2) a collimator size variable C, (3) a gantry initial angle variable $\theta_i$, (4) a gantry end angle variable $\theta_e$, (5) a couch angle variable $\phi$, (6) a predefined target volume point variable P, and (7) an arc variable a being a function of t, C, $\theta_i$, $\theta_e$, $\phi$ and the predefined clinical objective comprises the expression:

Minimize $$\sum_{P \in PTV} f_P$$

Subject to the constraints $$\sum_{a=1}^{N_A} D_{P,a} w_a - f_P = PRDOSE \quad P \in PTV$$

$$w_{a_j} \le M_{a_j} t_j \quad a_j \in \{1, \ldots, N_A\}, j \in \{1, \ldots, N_t\}$$

$$\sum_{j=1}^{N_t} t_j \le T$$

$$w_{a_j} \le N_{a_j} \phi_j \quad a_j \in \{1, \ldots, N_A\}, j \in \{1, \ldots, N_\phi\}$$

-continued $$\sum_{j=1}^{N_\phi} \phi_j \le \Phi$$

$$w_a \le R_a b_a \quad a \in \{1, \ldots, N_A\}$$

$$\sum_{a=1}^{N_A} b_a \le B$$

$$w_a, f_P \ge 0; t_j, \phi_j, b_a \in \{0, 1\}$$

wherein PRDOSE corresponds to the prescribed radiation dose for the predefined target volume PTV, T corresponds to a total number of target points in the predefined target volume, $\Phi$ corresponds to a predefined maximum number of couch angles permitted in the optimal treatment, B corresponds. to a predefined maximum number of beam configurations permitted in the optimal treatment plan, $M_{a_j}$, $N_{a_j}$, and $R_a$ corresponds to predefined positive constants representing the largest possible intensity emitted from an arc, $f_P$ corresponds to an amount of radiation exceeding the prescription dose at P, and $\omega_a$ corresponds to the intensity of an arc a, $D_{P,a}$ corresponds to a total dose deposited to P over all arcs, $L_P$ corresponds to a predefined lower bound for a radiation dose at P, and $U_P$ corresponds to a predefined upper bound for a radiation dose at P.

* * * * *

UNITED STATES PATENT AND TRADEMARK OFFICE
CERTIFICATE OF CORRECTION

PATENT NO.  : 6,546,073 B1
DATED       : April 8, 2003
INVENTOR(S) : Eva K. Lee

It is certified that error appears in the above-identified patent and that said Letters Patent is hereby corrected as shown below:

<u>Title page,</u>
Item [57], ABSTRACT,
Lines 10, 13, 18 and 21, delete "dose calculation" and replace with -- treatment plan --.

Signed and Sealed this

Twenty-sixth Day of August, 2003

JAMES E. ROGAN
*Director of the United States Patent and Trademark Office*